United States Patent
Kawaguchi (10) Patent No.: US 6,878,273 B2
(45) Date of Patent: Apr. 12, 2005

(54) DIALYZING APPARATUS

(75) Inventor: Keizoh Kawaguchi, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/086,836

(22) Filed: Mar. 4, 2002

(65) Prior Publication Data

US 2003/0000873 A1 Jan. 2, 2003

(30) Foreign Application Priority Data

Jul. 2, 2001 (JP) ......................................... 2001-200823

(51) Int. Cl.$^7$ ......................... B01D 61/28; B01D 61/32; A61M 1/14
(52) U.S. Cl. ..................... 210/321.65; 210/85; 210/90; 210/96.1; 210/97; 210/102; 210/109; 210/134; 210/143; 600/485; 600/495; 600/500; 600/546; 604/4.01; 604/30; 604/31
(58) Field of Search ........................... 210/85, 90, 96.1, 210/97, 102, 109, 134, 143, 321.65; 600/485, 495, 500, 546; 604/4.01, 30, 31

(56) References Cited

U.S. PATENT DOCUMENTS

| | | |
|---|---|---|
| 4,718,891 A | 1/1988 | Lipps .......................... 604/31 |
| 5,871,450 A | 2/1999 | Nomura et al. |
| 6,200,485 B1 | 3/2001 | Kitaevich et al. ........... 210/739 |

FOREIGN PATENT DOCUMENTS

| | | |
|---|---|---|
| EP | 0 686 404 A1 | 12/1995 |
| EP | 0 956 817 A1 | 11/1999 |
| GB | 2 246 718 A | 2/1992 |
| JP | 05-285128 | 11/1993 |
| JP | 10/165380 | 6/1998 |

*Primary Examiner*—John Kim
(74) *Attorney, Agent, or Firm*—Oliff & Berridge, PLC (57) ABSTRACT

A dialyzing apparatus includes a dialyzer which removes water from blood of a patient at a pre-set water-remove rate, an autonomic-nerve-activity-related-information obtaining device which obtains autonomic-nerve-activity-related information that is related to an activity of an autonomic nerve of the patient, and a water-remove-rate display device which displays a target water-remove rate based on the autonomic-nerve-activity-related information obtained by the autonomic-nerve-activity related-information obtaining device.

12 Claims, 6 Drawing Sheets

DIALYZING APPARATUS

BACKGROUND OF THE INVENTION

1. Field of the Invention

The present invention relates to a dialyzing apparatus which can quickly remove water from blood of a patient who may have arteriosclerosis, without causing an abrupt blood-pressure decrease in the patient.

2. Related Art Statement

There is known a dialyzing apparatus which artificially removes, by utilizing osmotic-pressure difference or ultrafiltration, urea, uric acid, or creatinine, together with water, from blood of a patient. When the dialyzing apparatus is used, a patient whose blood circulates through the apparatus, and a doctor who attends to the patient cannot move away from the apparatus, for at least several hours. Therefore, it is desired to increase the water-remove rate and thereby quickly finish the dialysis operation. However, if the water-remove rate is excessively high, the patient may fall in a shock. To avoid this, an appropriate water-remove rate is manually set to obtain a target water amount to be removed for a dialysis duration of from 4 to 5 hours, in view of a standard body weight and a measured body weight of the patient and a water-remove capacity. The water-remove rate is defined as an amount of fluid that permeates per unit time from the blood of the patient into the dialyzing fluid present in the dialyzer through the dialysis membrane, and the amount of fluid can be changed by changing a pressure difference over the dialysis membrane, e.g., a rotation speed of a negative-pressure pump which produces the pressure difference over the dialysis membrane.

Meanwhile, softness of arteries of a patient who has arteriosclerosis is low and accordingly, during a dialysis operation, blood pressure of the patient may abruptly decrease and fall in a shock. However, since it has been a conventional practice to set a water-remove rate irrespective of whether a patient has arteriosclerosis, there have been a considerably large number of cases where a patient who has arteriosclerosis fall in a shock during a dialysis operation.

SUMMARY OF THE INVENTION

It is therefore an object of the present invention to provide a dialyzing apparatus which can prevent a patient who may have arteriosclerosis, from falling in a shock during a dialysis operation.

In the above-described background, the Inventor has carried out extensive studies and has found the facts that the activity of autonomic nerve of a living subject is closely related to the blood pressure or arteriosclerosis degree of the subject and that an appropriate water-remove rate of a dialyzing apparatus can be determined based on autonomic-nerve-activity-related information that is related to the activity of autonomic nerve of the subject, so that water can be removed quickly from blood of the subject who may have arteriosclerosis, without causing the subject to fall in a shock during a dialysis operation. The present invention has been developed based on this finding.

According to a first aspect of the present invention, there is provided a dialyzing apparatus comprising a dialyzer which removes water from blood of a patient at a pre-set water-remove rate; an autonomic-nerve-activity-related-information obtaining device which obtains autonomic-nerve-activity-related information that is related to an activity of an autonomic nerve of the patient; and a water-remove-rate display device which displays a target water-remove rate based on the autonomic-nerve-activity-related information obtained by the autonomic-nerve-activity-related-information obtaining device.

Since the water-remove-rate display device displays the target water-remove rate based on the autonomic-nerve-activity-related information of the patient, the patient who may have arteriosclerosis can be prevented from falling in a shock during a dialysis operation, if the target water-remove rate displayed by the display device is set on the dialyzing apparatus. Thus, water can be quickly removed from blood of a patient who has arteriosclerosis, without causing an abrupt blood-pressure decrease in the patient.

According to a preferred feature of the first aspect of the present invention, the dialyzing apparatus further comprises a target-water-remove-rate determining means for determining the target water-remove rate based on the autonomic-nerve-activity-related information obtained by the autonomic-nerve-activity-related-information obtaining device, and the water-remove-rate display device displays the target water-remove rate determined by the target-water-remove-rate determining means. Since an operator of the dialyzing apparatus, such as a doctor, sets the target water-remove rate displayed by the display device, a patient who may have arteriosclerosis can be prevented from falling in a shock during a dialysis operation. Thus, water can be quickly removed from blood of a patient who has arteriosclerosis, without causing an abrupt blood-pressure decrease in the patient.

According to another preferred feature of the first aspect of the present invention, the autonomic-nerve-activity-related information may comprise at least one of a low-frequency component of fluctuations of blood-pressure values of the patient, a high-frequency component of fluctuations of pulse-period values of the patient, and a pressoreceptor-reflex sensitivity defined as a ratio of one of the low-frequency component and the high-frequency component to the other of the low-frequency component and the high-frequency component. Preferably, the target-water-remove-rate determining means determines a lower target water-remove rate range corresponding to a smaller low-frequency component of fluctuations of blood-pressure values of the patient, a greater high-frequency component of fluctuations of pulse-period values of the patient, and/or a smaller pressoreceptor-reflex sensitivity of the patient. Thus, an appropriate target water-remove rate corresponding to a degree of arteriosclerosis of the patient can be determined.

According to another preferred feature of the first aspect of the present invention, the target-water-remove-rate determining means determines, in a two-dimensional coordinate system which is defined by a first axis indicative of autonomic-nerve-activity-related information and a second axis indicative of water-remove rate, the target water-remove rate based on the obtained autonomic-nerve-activity-related information according to a predetermined relationship between autonomic-nerve-activity-related information and water-remove rate. Thus, an appropriate target water-remove rate corresponding to a degree of arteriosclerosis of the patient can be determined.

Preferably, the autonomic-nerve-activity-related information may be obtained during a dialysis operation, e.g., immediately after the commencement of the dialysis operation but, preferably, the information is obtained before the commencement of the dialysis operation, most preferably, immediately before the commencement.

According to a second aspect of the present invention, there is provided a dialyzing apparatus comprising a dialyzer which removes water from blood of a patient at a pre-set water-remove rate; an autonomic-nerve-activity-related-information obtaining device which obtains autonomic-nerve-activity-related information that is related to an activity of an autonomic nerve of the patient; and a water-remove-rate changing means for changing the pre-set water-remove rate to a target water-remove rate based on the autonomic-nerve-activity-related information obtained by the autonomic-nerve-activity-related-information obtaining device.

Since the water-remove-rate changing means automatically changes the pre-set water-remove rate to the target water-remove rate based on the autonomic-nerve-activity-related information of the patient, the patient who may have arteriosclerosis can be prevented from falling in a shock during a dialysis operation. Thus, water can be quickly removed from the blood of the patient, without causing an abrupt blood-pressure decrease in the patient.

According to a preferred feature of the second aspect of the present invention, the dialyzing apparatus further comprises a target-water-remove-rate determining means for determining the target water-remove rate based on the autonomic-nerve-activity-related information obtained by the autonomic-nerve-activity-related-information obtaining device, and the water-remove-rate changing means changes the pre-set water-remove rate to the target water-remove rate determined by the target-water-remove-rate determining means. Since the pre-set water-remove rate is automatically changed to the target water-remove rate based on the autonomic-nerve-activity-related information of the patient, the patient who may have arteriosclerosis can be prevented from falling in a shock during a dialysis operation. Thus, water can be quickly removed from the blood of the patient, without causing an abrupt blood-pressure decrease in the patient.

According to another preferred feature of the second aspect of the present invention, the target-water-remove-rate determining means determines a target water-remove rate range based on the autonomic-nerve-activity-related information comprising at least one of a low-frequency component of fluctuations of blood-pressure values of the patient, a high-frequency component of fluctuations of pulse-period values of the patient, and a pressoreceptor-reflex sensitivity defined as a ratio of one of the low-frequency component and the high-frequency component to the other of the low-frequency component and the high-frequency component, and the water-remove-rate changing means changes the pre-set water-remove rate to a value falling within the determined target water-remove-rate range. Since the pre-set water-remove rate is automatically changed to the target water-remove rate range based on at least one of the low-frequency component of fluctuations of blood-pressure values of the patient, the high-frequency component of fluctuations of pulse-period values of the patient, and the pressoreceptor-reflex sensitivity of the patient, the patient who may have arteriosclerosis can be prevented from falling in a shock during a dialysis operation. Thus, water can be quickly removed from the blood of the patient, without causing an abrupt blood-pressure decrease in the patient. Since pulse-wave-propagation-velocity-related-information such as pulse-wave propagation velocity itself or pulse-wave propagation time measured to determine the velocity changes with blood pressure of the patient, a low-frequency component of fluctuations of the pulse-wave-propagation-velocity-related-information may be obtained as the low-frequency component of fluctuations of blood-pressure values of the patient.

According to another preferred feature of the second aspect of the present invention, the target-water-remove-rate determining means determines a lower target water-remove rate range based on the autonomic-nerve-activity-related information comprising at least one of a greater low-frequency component of fluctuations of blood-pressure values of the patient, a smaller high-frequency component of fluctuations of pulse-period values of the patient, and a smaller pressoreceptor-reflex sensitivity of the patient. Since the pre-set water-remove rate is automatically changed to a lower target water-remove rate range based on a smaller low-frequency component of fluctuations of blood-pressure values of the patient, a greater high-frequency component of fluctuations of pulse-period values of the patient, and/or a smaller pressoreceptor-reflex sensitivity of the patient, the patient who may have arteriosclerosis can be prevented from falling in a shock during a dialysis operation. Thus, water can be quickly removed from the blood of the patient, without causing an abrupt blood-pressure decrease in the patient.

According to another preferred feature of the second aspect of the present invention, the target-water-remove-rate determining means determines, in a two-dimensional coordinate system which is defined by a first axis indicative of autonomic-nerve-activity-related information and a second axis indicative of water-remove rate, the target water-remove rate range based on the obtained autonomic-nerve-activity-related information according to a predetermined relationship between autonomic-nerve-activity-related information and water-remove rate range. Thus, water can be quickly removed from blood of the patient who may have arteriosclerosis, without causing an abrupt blood-pressure decrease in the patient.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
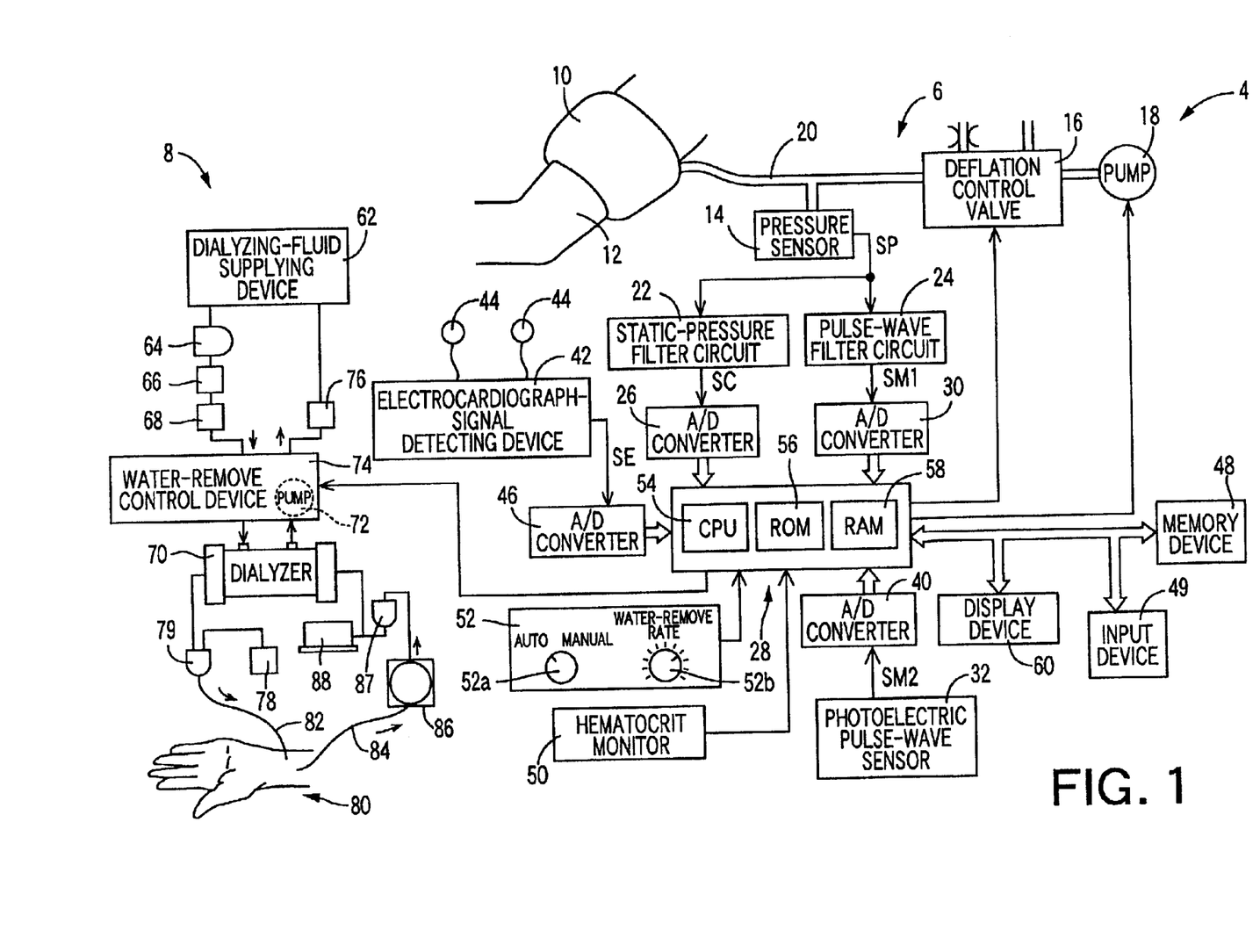
FIG. 1 is a diagrammatic view for explaining a construction of a dialyzing apparatus to which the present invention is applied.

Hereinafter, there will be described an embodiment of the present invention, by reference to the drawings. FIG. 1 is a diagrammatic view for explaining a construction of a dialyzing apparatus 4 to which the present invention is applied. The dialyzing apparatus 4 includes a measurement section 6 and a blood dialysis section 8. First, the measurement section 6 will be described below.

In FIG. 1, reference numeral 10 designates a blood-pressure measuring cuff which includes a belt-like cloth bag and a rubber bag accommodated in the cloth bag and which is wound around an upper portion 12 of one arm of a patient that is not connected to a dialyzer 70, described later. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure PK in the cuff 10, and supplies a pressure signal SP representing the detected pressure PK, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff pressure signal SC representing the static or pressing pressure in the cuff 10. The cuff pressure signal SC is supplied to a control device 28 via an A/D (analog-to-digital) converter 26. The pulse-wave filter circuit 24 includes a band-pass filter and extracts, from the pressure signal SP, an oscillating component that is produced in synchronism with heartbeat of the patient, i.e., a cuff-pulse-wave signal SM1. The cuff-pulse-wave signal SM1 is supplied to the control device 28 via an A/D converter 30.

Figure 2:
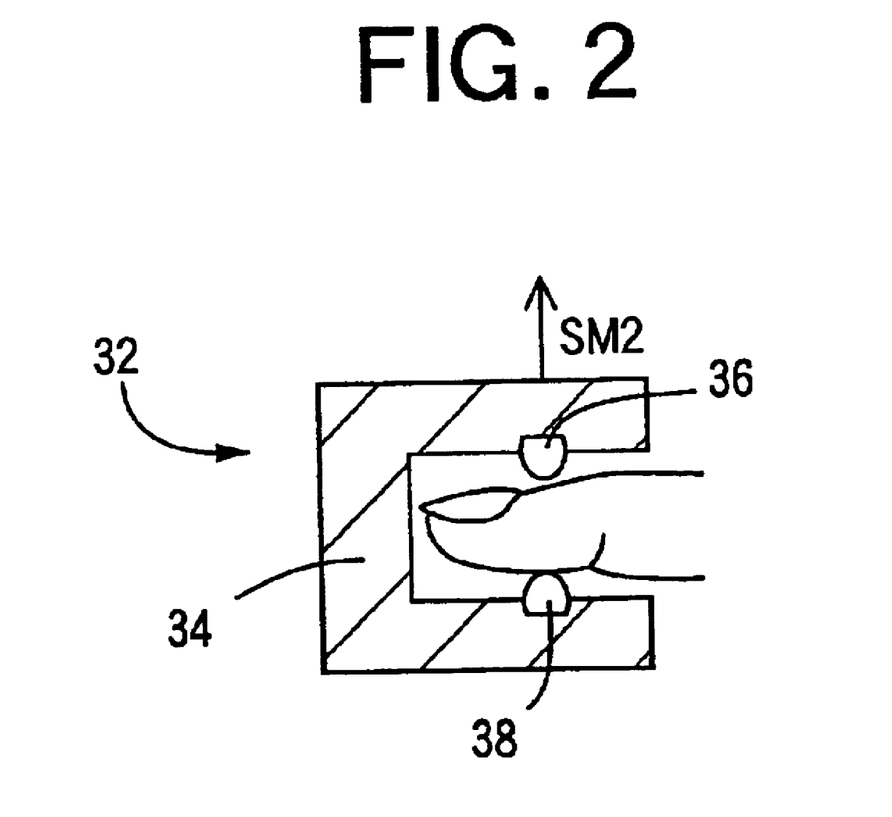
FIG. 2 is a cross-sectional view showing a construction of a photoelectric pulse-wave sensor of the apparatus of FIG. 1.

A photoelectric pulse-wave sensor 32 functions as a volumetric-pulse-wave detecting device. The sensor 32 detects a volumetric pulse wave (i.e., a plethysmograph) representing a volume of blood present in peripheral blood vessels of a living subject. The sensor 32 is worn on, e.g., an end portion of a finger of the other arm than the arm around which the cuff 10 is wound. The photoelectric pulse-wave sensor 32 has the same construction as that of a known sensor used to detect pulse rate or oxygen saturation. As shown in detail in FIG. 2, the sensor 32 includes a housing 34 that can accommodate a portion of a living subject, such as an end portion of a finger; a light emitting element 36 as a light source that is disposed on one of opposite walls of the housing 34 and emits, toward skin of the subject, a red or infrared light in a wavelength range that can be reflected by hemoglobin, preferably a light having a wavelength of, e.g., about 800 nm, that is not influenced by blood oxygen saturation; and a light receiving element 38 that is disposed on the other wall of the housing 34 such that the light receiving element 38 is opposed to the light emitting element 36, and detects the light transmitted through the portion of the subject. The light receiving element 38 produces a photoelectric-pulse-wave signal SM2 representing the detected amount of light, i.e., volume of blood present in capillaries of the portion of the subject, and supplies the photoelectric-pulse-wave signal SM2 to the control device 28 via an A/D converter 40.

An electrocardiograph-signal detecting device 42 continuously detects an electrocardiograph waveform WH, i.e., so-called electrocardiogram (ECG) representing an action potential of cardiac muscle of the subject, through a plurality of electrodes 44 which are adhered to respective prescribed locations of the subject, and supplies an electrocardiograph signal SE representing the detected electrocardiograph waveform WH, to the control device 28 via an A/D converter 56.

A memory device 48 is provided by a well known memory means such as a RAM (random access memory), a magnetic-disc device (HDD), or a removable media (MO, DVD, etc.). The memory device 48 stores a relationship that is used to determine an estimated blood pressure, and a relationship that is used to determine a target water-remove rate. An input device 49 includes various keys that are manually operable by an operator to input an identification (ID) code, a standard body weight, and a measured body weight, of the patient and supply those data to the control device 28. A hematocrit monitor 50 optically measures, during a blood dialysis operation, a hematocrit (red-blood-cell volume percentage %) of the patient, from blood of the patient. A water-remove-rate setting device 52 includes a mode-switch dial 52a that is manually operable to select a manual ("MANUAL") mode or an automatic ("AUTO") mode, and a water-remove-rate dial 52b that is manually operable to set an appropriate water-remove rate of the dialyzer 70. The manual mode allows an operator to manually set a water-remove rate through the water-remove-rate dial 52b, and the automatic mode allows the dialyzing apparatus 4 to automatically set a water-remove rate.

The control device 28 is provided by a so-called microcomputer including a CPU (central processing unit) 54, a ROM (read only memory) 56, a RAM 58, and an I/O port, not shown. The CPU 54 processes signals according to the control programs pre-stored in the ROM 56 by utilizing the temporary-storage function of the RAM 58, and controls the deflation control valve 16 and the air pump 18. In addition, the CPU 54 operates for determining a blood-pressure value BP of the patient, successively determining estimated blood-pressure values EBP of the patient, judging an abnormality of the blood-pressure of the patient during a blood dialysis operation, controlling the water-remove rate, and controlling what is displayed by a display device 60. Moreover, the CPU 54 controls respective rotation speeds of a negative-pressure pump 72 of a water-remove control device 74 and a blood-circulation pump 86 of the blood dialysis section 8 that will be described later.

Next, the blood dialysis section 8 will be described. The blood dialysis section 8 has a construction similar to that of a common dialyzing device. More specifically described, the blood dialysis section 8 includes a dialyzing-fluid circulation system as a closed circuit that includes a dialyzing-fluid supplying device 62; a constant-flow-rate valve 64 which adjusts the dialyzing fluid such that the fluid flows at a constant flow rate; a gas-remove tank 66; a warming device 68; the dialyzer 70; the water-remove control device 74 including the negative-pressure pump 72; and a blood-leakage sensor 76. The blood dialysis section 8 additionally includes a blood circulation system as a closed circuit that includes a drip chamber 79 that is connected to the dialyzer 70 and a venous-pressure sensor 78; a tube 82 that is connected to a vein of the patient; a tube 84 that is connected to an artery of the patient; the blood-circulation pump 86; a drip chamber 87; and a heparin injecting pump 88. The dialyzing-fluid supplying device 62 has the function of preparing a dialyzing fluid by mixing a concentrated fluid with water at a prescribed ratio. The warming device 68 keeps the prepared dialyzing fluid at a prescribed temperature. The negative-pressure pump 72 produces a negative pressure in a space between the pump 72 and the supplying device 62, thereby introducing the dialyzing fluid accumulating in the supplying device 62, into the dialyzer 70. The negative-pressure pump 72 additionally adjusts a water-remove rate. The heparin injecting pump 88 injects, little by little, heparin as an anticoagulant into the circulating blood during a blood dialysis operation.

The dialyzer 70 employs a dialysis membrane that is formed of a cellulose material such as regenerated cellulose or acetic cellulose, or a macromolecular material such as polyacrylonitrile copolymer or polymethyl methacrylate, so that the blood and the dialyzing fluid contact each other via the dialysis membrane. Thus, owing to diffusion effect and ultrafiltration effect, waste products and water are moved from the blood of the patient into the dialyzing fluid, and necessary electrolytes are moved from the dialyzing fluid into the blood. The water-remove rate is defined as a difference between the controlled fluid flow-in rate and the fluid flow-out rate, and is expressed as an amount of water removed per unit time, Wv (1/h). The water-remove rate may be controlled by controlling, e.g., a pressure difference over the dialysis membrane, or controlling a rotation speed of the negative-pressure pump 72 that produces the pressure difference.

Figure 3:
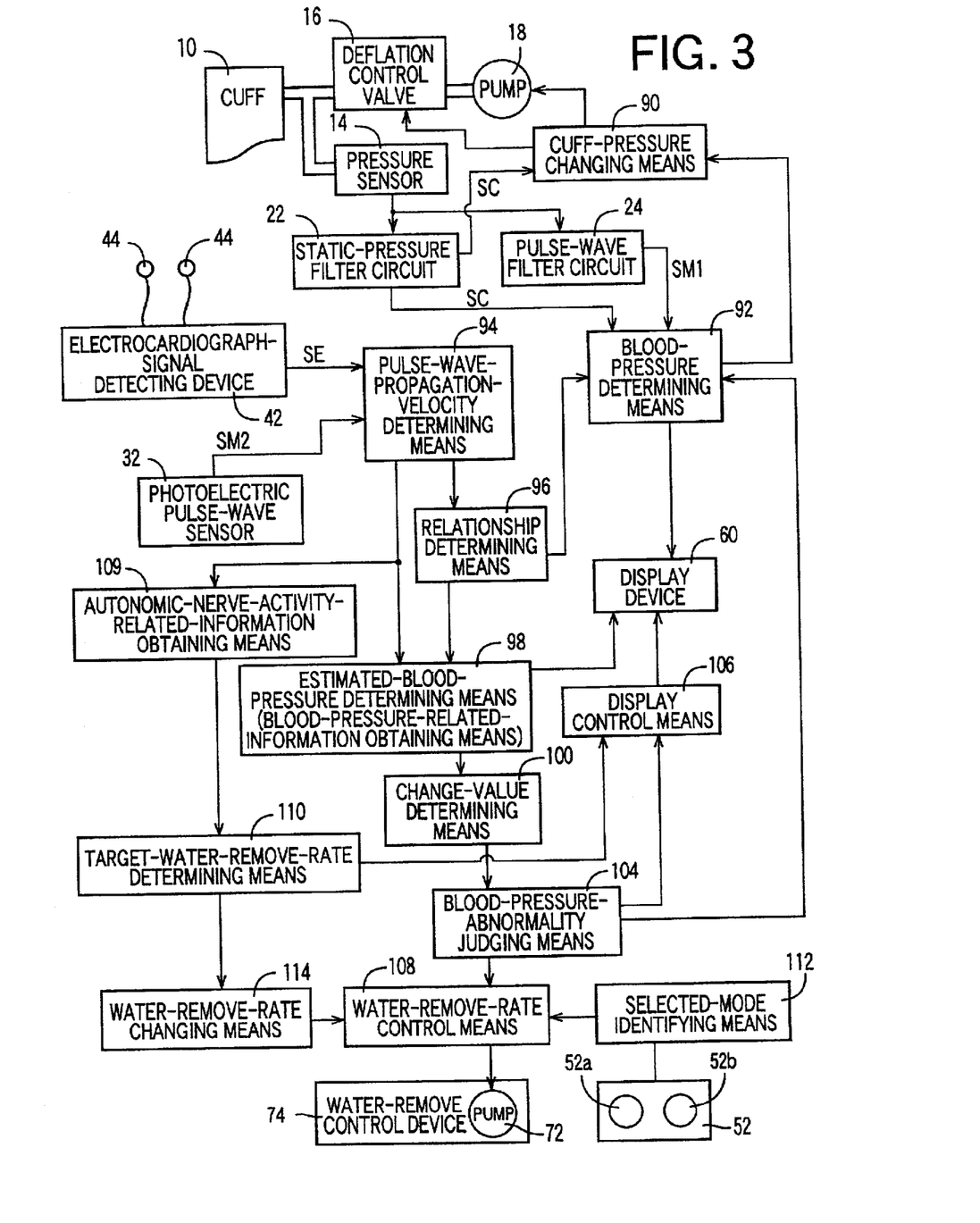
FIG. 3 is a block diagram for explaining essential control functions of a control device of the apparatus of FIG. 1.

FIG. 3 is a block diagram for explaining essential functions of the control device 28. A cuff-pressure changing means 90 and a blood-pressure determining means 92 are operated for carrying out a blood-pressure measuring operation, each time a prescribed blood-pressure-measurement period TB, e.g., several tens of minutes to one hour, passes.

The cuff-pressure changing means 90 operates, based on the cuff pressure signal SC supplied from the static-pressure filter circuit 22, the air pump 18 and the deflation control valve 16 to quickly increase the pressing pressure of the cuff 10, i.e., the cuff pressure PC up to a prescribed target pressure (e.g., 180 mmHg) which would be higher than a systolic blood-pressure value $BP_{SYS}$ of the patient and subsequently slowly decrease the cuff pressure PC at a rate of from 2 to 3 mmHg/sec. After the blood-pressure determining means 92, described below, has determined a blood-pressure value BP of the patient, the cuff-pressure changing means 90 quickly decreases the cuff pressure PC down to atmospheric pressure. The blood-pressure determining means 92 determines a systolic, a mean, and a diastolic blood-pressure value $BP_{SYS}$, $BP_{MEAN}$, $BP_{DIA}$ of the upper arm 12 of the patient, according to well-known oscillometric method, based on the cuff-pressure signal SC continuously supplied from the static-pressure filter circuit 22, and the cuff-pulse-wave signal SM1 continuously supplied from the pulse-wave filter circuit 24, each during the slow decreasing of the cuff pressure PC under the control of the cuff-pressure changing means 90. In addition, the blood-pressure determining means 92 operates the display device 60 to display the thus determined blood-pressure values $BP_{SYS}$, etc.

Figure 4:
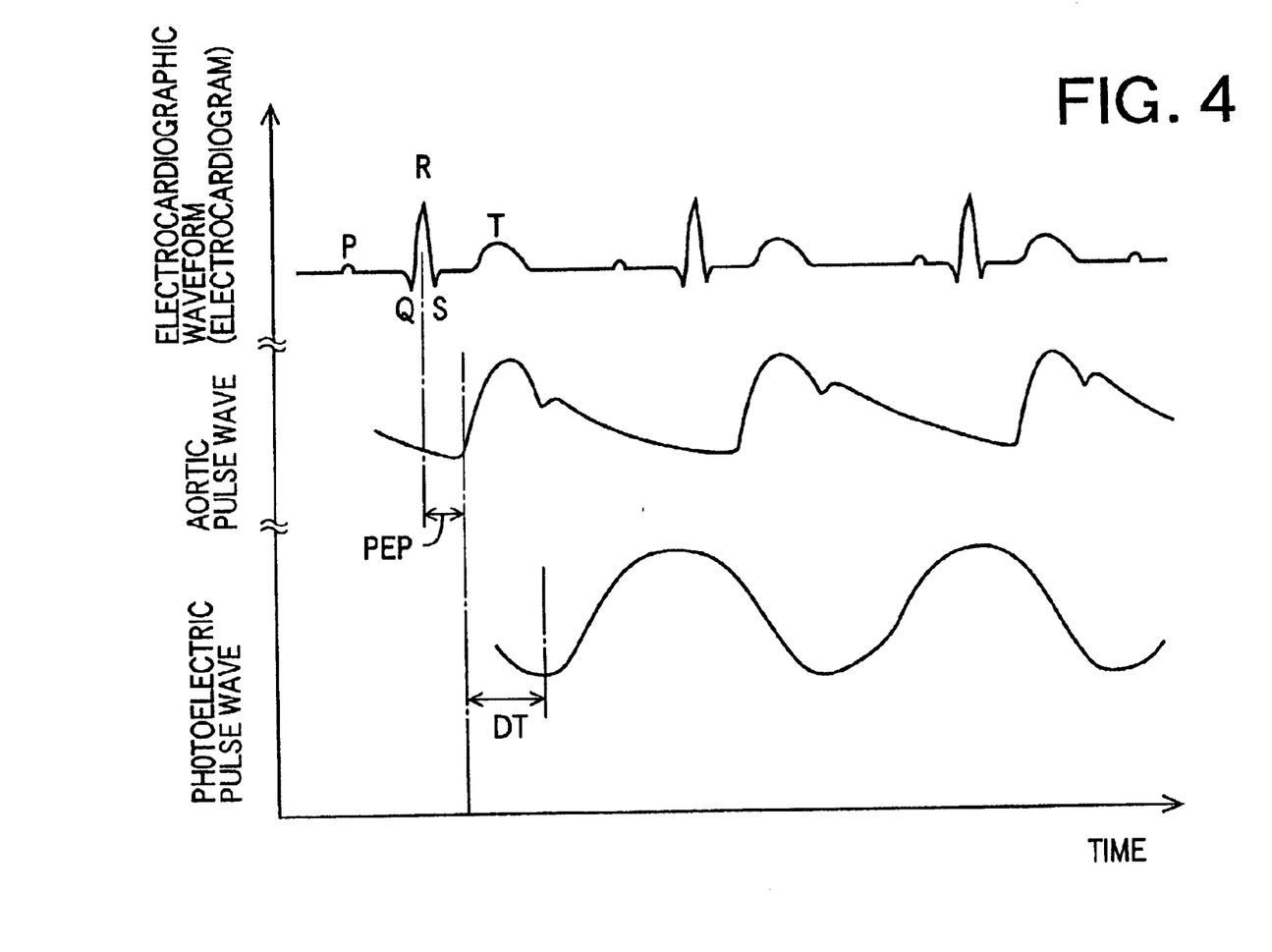
FIG. 4 is a graph for explaining a manner in which a pulse-wave propagation time DT is determined by a pulse-wave-propagation-velocity determining means shown in FIG. 3.

A pulse-wave-propagation-velocity determining means 94 successively determines, as illustrated in FIG. 4, a time difference DT (i.e., a pulse-wave propagation time) between a periodic point (e.g., an R-wave) on each of successive heartbeat-synchronous pulses of the electrocardiographic waveform continuously detected by the electrocardiograph-signal detecting device 42, and a periodic point (e.g., a rising or minimal point) on a corresponding one of successive heartbeat-synchronous pulses of the photoelectric pulse wave continuously detected by the photoelectric pulse-wave sensor 32. The determining means 94 successively determines, based on each of the pulse-wave propagation times DT successively determined for the successive heartbeat-synchronous pulses, a pulse-wave-propagation velocity PWV (m/sec) at which a pulse wave propagates through an artery of the patient, according to the following Expression 1 pre-stored in the ROM 56:

$$PWV = L/(DT - PEP) \qquad \text{(Expression 1)}$$

where L (m) is a distance from the left ventricle of the heart, via the aorta, to a position where the sensor 32 is worn on the patient, and PEP (sec) is a pre-ejection period between an R-wave of the electrocardiographic waveform and a rising point of an aortic pulse wave. The distance L (m) is a value actually measured from the patient, or a value converted from a height of the patient, and the pre-ejection period PEP is a value actually measured from the patient, a statistically obtained value, or a value experimentally obtained in advance from the patient.

The pulse-wave propagation time DT, or the pulse-wave propagation velocity PWV determined from the time DT, increases as the blood pressure, or the degree of arteriosclerosis, of the patient increases. Therefore, the time DT or the velocity PWV can be said as a mathematical function of blood pressure or degree of arteriosclerosis. For example, providing that a pulse-wave propagation velocity PWV corresponding to a prescribed blood pressure (e.g., 80 mmHg) is defined as a normalized pulse-wave propagation velocity $PWV_N$, the normalized pulse-wave propagation velocity $PWV_N$ increases as the degree of arteriosclerosis increases. Thus, the normalized pulse-wave propagation velocity $PWV_N$ can be used as very useful arteriosclerosis-related information. The pulse-wave propagation velocity PWV can be used as the normalized pulse-wave propagation velocity $PWV_N$.

A relationship determining means 96 determines coefficients α, β of the following Expression 2 representing a relationship between estimated blood pressure EBP and pulse-wave-propagation velocity PWV, based on one of systolic, mean, and diastolic blood-pressure values $BP_{SYS}$, $BP_{MEAN}$, $BP_{DIA}$ determined by the blood-pressure determining means 92 in a blood-pressure measuring operation, and the pulse-wave-propagation velocity PWV determined by the pulse-wave-propagation-velocity determining means 94 during the blood-pressure measuring operation, or immediately before or after the measuring operation. For example, the coefficients α, β of the Expression 2 are determined based on a first pair of a systolic blood pressure $BP_{SYS}$ determined by the blood-pressure determining means 92 in the current blood-pressure measuring operation and a pulse-wave propagation velocity PWV determined during the current measuring operation, and a second pair of a systolic blood pressure $BP_{SYS}$ determined by the means 92 in the last blood-pressure measuring operation and a pulse-wave propagation velocity PWV determined during the last measuring operation.

$$EBP = \alpha(PWV) + \beta \qquad \text{(Expression 2)}$$

where α and β are positive constants.

If the systolic blood-pressure values $BP_{SYS}$ determined by the blood-pressure determining means 92 are used to determine the coefficients of the above-indicated Expression 2, Expression 2 provides estimated systolic blood-pressure values $EBP_{SYS}$; if the mean blood-pressure values $BP_{MEAN}$ determined by the means 92 are used to determine the coefficients of Expression 2, Expression 2 provides estimated mean blood-pressure values $EBP_{MEAN}$; and if the diastolic blood-pressure values $BP_{DIA}$ determined by the means 92 are used to determine the coefficients of Expression 2, Expression 2 provides estimated diastolic blood-pressure values $EBP_{DIA}$. Which sort of blood-pressure values out of the systolic, mean, and diastolic blood-pressure values $BP_{SYS}$, $BP_{MEAN}$, $BP_{DIA}$ determined by the means 92 are selected to determine Expression 2, depends upon which sort of blood-pressure values out of systolic, mean, and diastolic blood-pressure values are continuously monitored as estimated blood-pressure values EBP.

An estimated-blood-pressure determining means 98 functioning as a blood-pressure-related-information obtaining means, successively and non-invasively determines, according to Expression 2 whose coefficients α, β have been determined by the relationship determining means 96, an estimated blood-pressure value EBP of the patient based on each of the pulse-wave-propagation velocities PWV successively determined by the wave-propagation-velocity determining means 94. In addition, the determining means 98 operates the display device 60 to display a time-wise change of the successively determined, estimated blood-pressure values EBP. Preferably, a period at which the determining means 98 determines an estimated blood-pressure value EBP is as short as the period of one heartbeat or several heartbeats, but it may be considerably long if it is shorter than the blood-pressure-measurement period TB of the blood-pressure determining means 92.

A change-value determining means 100 successively determines a change value of each of the estimated blood-pressure values EBP successively determined by the estimated-blood-pressure determining means 98. An estimated-blood-pressure change value means a rate of change, or an amount of change, of each of the successively determined, estimated blood-pressure values EBP from a reference estimated blood-pressure value EBP. The reference estimated blood-pressure value EBP may be an estimated blood-pressure value EBP determined when the current relationship (i.e., the current coefficients of Expression 2) is determined by the relationship determining means 96, that is, the blood-pressure value BP determined by the blood-pressure determining means 92.

A blood-pressure-abnormality judging means 104 judges that a lowering of the blood pressure of the patient is abnormal, when the estimated-blood-pressure change value determined by the change-value determining means 100 is greater than one of a plurality of abnormality-judgment threshold values, selected for the patient by a selecting means (not shown), that corresponds to a time duration which has elapsed from a commencement of the current blood dialysis operation. When the judging means 104 judges that the blood pressure of the patient is abnormal, the judging means 104 operates a display control means 106 to control the display device 60 to indicate the abnormality, and additionally operates the cuff-pressure changing means 90 and the blood-pressure determining means 92 to measure, using the cuff 10, reliable blood-pressure values BP of the patient.

A water-remove-rate control means 108 controls the water-remove control device 74 so that the dialyzer 70 removes water at the water-remove rate Wv (1/h) set by the water-remove-rate dial 52b of the water-remove-rate setting device 52. Since the hematocrit (i.e., red-blood-cell volume percentage %) of blood of the patient increases as the blood dialysis (or water removal) advances, the water-remove rate is gradually decreased as time elapses from the commencement of the current dialysis operation or as the hematocrit increases. In addition, the water-remove-rate control means 108 decreases, by a prescribed value, the water-remove rate effective in the blood dialysis section 8, or even stops the current water-removing operation, if the blood-pressure-abnormality judging means 104 judges that a lowering of the blood pressure of the patient is abnormal.

An autonomic-nerve-activity-related-information obtaining means 109 obtains autonomic-nerve-activity-related information that is related to an activity of the autonomic nerve of the patient. The autonomic-nerve-activity-related information may be a low-frequency component of the fluctuations of blood-pressure values of the patient, a high-frequency component of the fluctuations of pulse-period values of the patient, or a pressoreceptor-reflex sensitivity defined as a ratio of one of the high-frequency component and the low-frequency component to the other of the two components. The low-frequency component of the fluctuations of blood-pressure values of the patient may be obtained as a 0.04 to 0.15 Hz signal component, DTLF, of the fluctuations of respective pulse-wave-propagation velocity values PWV or respective pulse-wave propagation time values DT that correspond to respective blood-pressure values determined in synchronism with respective heartbeats of the patient. The frequency of signal component DTLF is sufficiently lower than a respiration frequency of the patient, and each component value is iteratively determined by well-known fast Fourier transform method or autoregression method. The high-frequency component of the fluctuations of pulse-period values of the patient may be obtained as a 0.15 to 0.4 Hz signal component, RRHF, of fluctuations of the respective intervals (i.e., pulse periods) of successive R-waves of the electrocardiograph signal SE that are determined in synchronism with the respective heartbeats of the patient. The frequency of signal component RRHF is in the vicinity of the respiration frequency of the patient, and each component value is iteratively determined by the fast Fourier transform method or autoregression method. The low-frequency signal component DTLF and the high-frequency signal component RRHF provide a sympathetic-nerve index and a parasympathetic-nerve index, respectively, and the above-indicated pressoreceptor-reflex sensitivity may be defined as a ratio (=RRHF/DTLF) of the high-frequency signal component RRHF to the low-frequency signal component DTLF.

Figure 5:
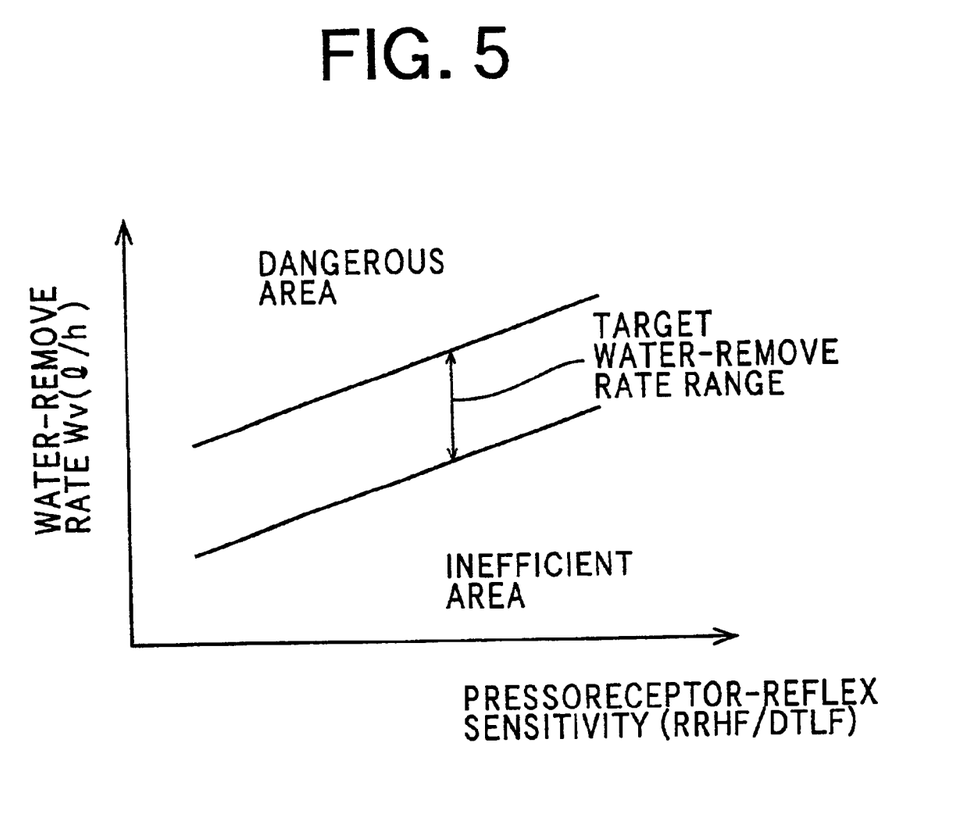
FIG. 5 is a view showing a pre-stored relationship which is utilized by a target-water-remove-rate determining means shown in FIG. 3 to determine a target water-remove rate range.

A target-water-remove-rate determining means 110 determines a target water-remove rate range, based on the autonomic-activity-related information obtained by the autonomic-activity-related-information obtaining means 109, i.e., at least one of the sympathetic-nerve index DTLF, the parasympathetic-nerve index RRHF, and the pressoreceptor-reflex sensitivity (RRHF/DTLF), the measured body weight of the patient, the standard body weight of the patient that is determined based on the height of the patient that is input through the input device 49, and/or a prescribed water-remove-rate capability of the dialyzer 70, according to a prescribed relationship between the parameter or parameters and target water-remove rate range. The prescribed relationship provides that as the low-frequency component DTLF of fluctuations of the pulse-wave propagation times DT decreases, the target water-remove rate decreases; that as the high-frequency component RRHF of fluctuations of the pulse periods increases, the target water-remove rate decreases; or that as the pressoreceptor-reflex sensitivity (RRHF/DTLF) decreases, the target water-remove rate decreases. FIG. 5 shows, as an example of the prescribed relationship, a prescribed relationship between pressoreceptor-reflex sensitivity (RRHF/DTLF) and target water-remove rate range, wherein as arteriosclerosis advances, i.e., pressoreceptor-reflex sensitivity (RRHF/DTLF) decreases, target water-remove rate range decreases, a dangerous area or range above the target rate range increases, and an insufficient area or range below the target rate range decreases. That is, the prescribed relationship is experimentally determined so that a dialysis operation can be finished as quickly as possible, without causing the patient to fall in a shock (i.e., an abrupt blood-pressure decrease). The relationship is pre-stored in the ROM 56.

The display control means 106 also functions as a water-remove-rate displaying means for operating the display device 60 to display the target water-remove rate range determined by the target-water-remove-rate determining means 110. In a state in which a selected-mode identifying means 112 identifies that the manual mode is selected, an operator such as a doctor can read, in at least an initial period of a blood dialysis operation, a target water-remove rate range, displayed on the display device 60, that corresponds to an actual pulse-wave propagation velocity PWV of a patient 80, and operates the water-remove rate dial 52b to set an appropriate water-remove rate falling within the displayed target water-remove rate range.

A water-remove-rate changing means 114 automatically changes the water-remove rate effective in the blood dialysis section 8, so as to be equal to a target water-remove rate determined based on the autonomic-activity-related information obtained by the autonomic-activity-related-information obtaining means 109, e.g., the sympathetic-nerve index DTLF, the parasympathetic-nerve index RRHF, or the pressoreceptor-reflex sensitivity (RRHF/DTLF). More specifically described, the water-remove-rate changing means 114 changes the water-remove rate controlled by the water-remove-rate control means 108 in the blood dialysis section 8, so as to be within the target water-remove rate range determined by the target-water-remove-rate determining means 110. For example, in a state in which the selected-mode identifying means 112 identifies that the automatic mode is selected, the changing means 114 automatically changes the water-remove rate set through the water-remove-rate dial 52b of the water-remove-rate setting device 52, so as to be a value within the target-water-remove-rate range corresponding to the autonomic-activity-related information obtained immediately before the commencement of the blood dialysis operation. Alternatively, the changing means 114 may automatically change an upper and a lower limit of a water-remove rate range that can be set through the water-remove-rate dial 52b of the water-remove-rate setting device 52, so as to be equal to an upper and a lower limit of the above-indicated target-water-remove-rate range.

Figure 6:
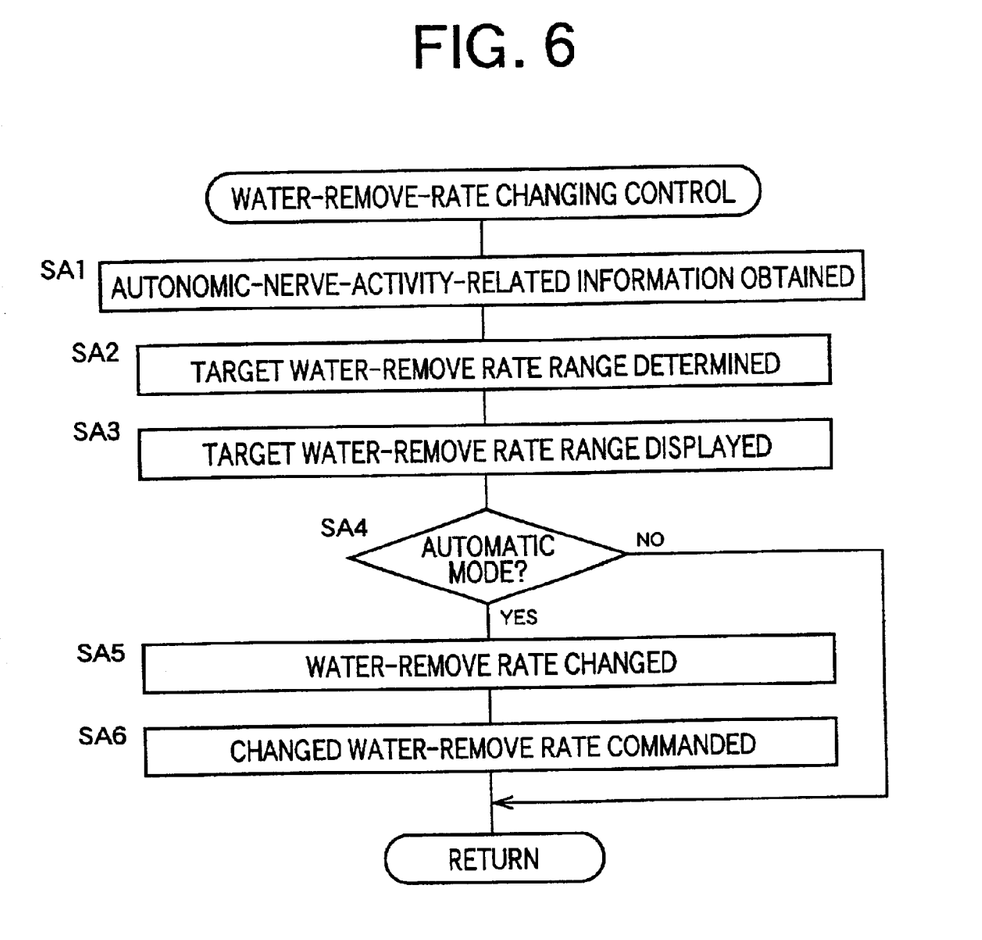
FIG. 6 is a flow chart representing a control program according to which the control device shown in FIG. 1 is operated.

FIG. 6 is a flow chart for explaining the essential control functions of the control device 28 that are periodically operated at a prescribed period of from several milliseconds to several tens of milliseconds.

In FIG. 6, at Step SA1 (hereinafter, "Step" is omitted, if appropriate) corresponding to the autonomic-nerve-activity-related-information obtaining means 109, the control device determines, e.g., an R-wave of each of heartbeat-synchronous pulses of the electrocardiographic waveform represented by the electrocardiograph signal SE, and a rising point of each of heartbeat-synchronous pulses of the photoelectric pulse wave represented by the photoelectric-pulse-wave signal SM2, and iteratively determines, as a pulse-wave propagation time DT, a time difference between the time of occurrence of the R-wave of each heartbeat-synchronous pulse and the time of occurrence of the rising point of the corresponding heartbeat-synchronous pulse, as illustrated in FIG. 4. In addition, the control device iteratively determines, as a pulse period, a time interval between respective R-waves of each pair of successive heartbeat-synchronous pulses of the electrocardiographic waveform. Moreover, the control device determines, by fast Fourier transform method or autoregression method, a 0.04 to 0.15 Hz signal component, i.e., low-frequency component DTLF of fluctuations of the pulse-wave propagation times DT determined in synchronism with the heartbeats of the patient, and determines a 0.15 to 0.4 Hz signal component, i.e., high-frequency component RRHF of fluctuations of the respective time intervals (pulse periods) of successive R-waves of the electrocardiograph signal that are determined in synchronism with the heartbeats of the patient, and finally determines a ratio of the high-frequency component RRHF to the low-frequency component DTLF as the pressoreceptor-reflex sensitivity (RRHF/DTLF). The low-frequency component DTLF and the high-frequency component RRHF provide respective pieces of autonomic-nerve-activity-related information that serve as a sympathetic nerve index and a parasympathetic nerve index, respectively. The pressoreceptor-reflex sensitivity (RRHF/DTLF) provides a piece of autonomic-nerve-activity-related information that serves as a sympathetic-parasympathetic nerve index.

Next, at SA2 corresponding to the target-water-remove-rate determining means 110, the control device determines, according to the pre-stored relationship shown in FIG. 5, a target water-remove rate range based on the pressoreceptor-reflex sensitivity (RRHF/DTLF) determined, preferably, immediately before the commencement of a dialysis operation. Then, the control goes to SA3 corresponding to the display control means 106. At SA3, the control device controls the display device 60 to display the target water-remove rate range determined at SA2, so that the target water-remove rate range displayed can be read by an operator such as a doctor.

Then, at SA4 corresponding to the selected-mode identifying means 112, the control device judges whether the automatic mode is selected as a result of operation of the mode-switch dial 52a of the water-remove-rate setting device 52. If a negative judgment is made at SA4, a current control cycle according to the flow chart of FIG. 6 is finished. On the other hand, if a positive judgment is made at SA4, the control goes to SA5 corresponding to the water-remove-rate changing means 114. At SA5, the control device changes the water-remove rate set by the water-remove-rate dial 52b, to a value within the target water-remove rate range determined at SA2. Then, the control goes to SA6 corresponding to the water-remove-rate control means 108, the control device commands the water-remove rate changed at SA4, so that the rotation speed of the negative-pressure pump 72 is so controlled as to operate the dialyzer 70 at the commanded water-remove rate.

As is apparent from the foregoing description of the preferred embodiment, in the state in which the dialyzing apparatus 4 is in the manual mode, the target water-remove rate determined based on the autonomic-nerve-activity-related information related to the degree of arteriosclerosis of the patient, is displayed on the display device 60. Therefore, if the operator sets, through the water-remove-rate dial 52b, a value equal to the target water-remove rate displayed on the display device 60, a patient who suffers arteriosclerosis can be effectively prevented from falling in a shock during a blood dialysis operation. Thus, water can be quickly removed from a patient having arteriosclerosis, without causing an abrupt blood-pressure decrease in the patient.

In the illustrated embodiment, the autonomic-nerve-activity-related-information obtaining means 109 (SA1)

obtains the autonomic-nerve-activity-related information (the low-frequency component DTLF, the high-frequency component RRHF, or the pressoreceptor-reflex sensitivity (RRHF/DTLF)), and the target-water-remove-rate determining means 110 (SA2) determines the target water-remove rate based on the obtained autonomic-nerve-activity-related information. The display control means 106 (SA3) controls the display device 60 to display the target water-remove rate determined by the target-water-remove-rate determining means 110. If the target water-remove rate displayed by the display device 60 is set by an operator such as a doctor through the water-remove-rate dial 52b, a patient who has arteriosclerosis can be effectively prevented from falling in a shock during a dialysis operation. Thus, water can be quickly removed from blood of a patient having arteriosclerosis, without causing an abrupt blood-pressure decrease in the patient.

In the illustrated embodiment, the target-water-remove-rate determining means 110 (SA2) determines the target water-remove rate range, based on the autonomic-nerve-activity-related information, the measured and standard body weights of the patient, and the prescribed water-remove-rate capability of the dialyzer 70, and the display control means 106 controls the display device 60 to display the determined target water-remove rate range. The target water-remove rate (range) decreases as the degree of arteriosclerosis of the patient 80 increases. That is, as the low-frequency component of fluctuations of the blood-pressure values of the patient 80 decreases, the target water-remove rate decreases; as the high-frequency component of fluctuations of the pulse periods of the patient 80 increases, the target water-remove rate decreases; or as the pressoreceptor-reflex sensitivity of the patient 80 decreases, the target water-remove rate decreases. Therefore, the water-remove-rate dial 52b is manually operated to set, within the target water-remove rate range displayed on the display device 60, an appropriate water-remove rate corresponding to the degree of arteriosclerosis of the patient. Thus, a patient who may have arteriosclerosis can be effectively prevented from falling in a shock during a blood dialysis operation, and water can be quickly removed from the patient, without causing an abrupt blood-pressure decrease in the patient.

In the illustrated embodiment, the target-water-remove-rate determining means 110 determines the target water-remove rate range based on the actual autonomic-nerve-activity-related information according to the prescribed relationship between autonomic-nerve-activity-related information and water-remove rate that assures that water can be removed from blood of the patient as quickly as possible without causing the patient to fall in a shock. Thus, an appropriate target water-remove rate corresponding to the degree of arteriosclerosis of the patient can be determined.

The present dialyzing apparatus 4 includes the dialyzer 70, and can control the water-remove rate at which water is removed from blood of a patient through the dialyzer 70, more specifically described, the present dialyzing apparatus 4 includes (a) the autonomic-nerve-activity-related-information obtaining means 109 (SA1) which obtains the autonomic-nerve-activity-related information that is related to the activity of autonomic serve of the patient, and (b) the target-water-remove-rate changing means 114 (SA5) which changes the current water-remove rate so as to be equal to the target water-remove rate determined based on the autonomic-nerve-activity-related information obtained by the autonomic-nerve-activity-related-information obtaining means 109. Since the current water-remove rate is automatically changed to the target water-remove rate determined based on the autonomic-nerve-activity-related information of the patient 80, a patient who has arteriosclerosis can be effectively prevented from falling in a shock during a blood dialysis operation. Thus, water can be quickly removed from blood of a patient having arteriosclerosis, without causing an abrupt blood-pressure decrease in the patient.

In addition, the present dialyzing apparatus 4 includes the autonomic-nerve-activity-related-information obtaining means 109 which obtains the autonomic-nerve-activity-related information, the target-water-remove-rate determining means 110 (SA2) determines the target water-remove rate based on the obtained autonomic-nerve-activity-related information, and the target-water-remove-rate changing means 114 automatically changes the current water-remove rate of the dialyzer 70, so as to be equal to the target water-remove rate determined by the determining means 110. Therefore, a patient who has arteriosclerosis can be effectively prevented from falling in a shock during a blood dialysis operation, and water can be quickly removed from blood of the patient, without causing an abrupt blood-pressure decrease in the patient.

Moreover, in the illustrated embodiment, the target-water-remove-rate determining means 110 determines the target water-remove rate range, based on at least one of the low-frequency component of fluctuations of the blood-pressure values of the patient, the high-frequency component of fluctuations of the pulse periods of the patient, and the pressoreceptor-reflex sensitivity, and the target-water-remove-rate changing means 114 automatically changes the current water-remove rate of the dialyzer 70 to a value within the thus determined water-remove rate range. That is, the current water-remove rate is automatically changed to a value within the target water-remove rate ranged determined based on at least one of the low-frequency component of fluctuations of the blood-pressure values of the patient, the high-frequency component of fluctuations of the pulse periods of the patient, and the pressoreceptor-reflex sensitivity. Thus, water can be quickly removed from a patient 80 having arteriosclerosis, without causing an abrupt blood-pressure decrease in the patient, i.e., causing the patient to fall in a shock during a dialysis operation.

In the illustrated embodiment, the target-water-remove-rate determining means 110 determines the target water-remove rate (range) such that as the low-frequency component of fluctuations of the blood-pressure values of the patient 80 increases, the target water-remove rate decreases; that as the high-frequency component of fluctuations of the pulse periods of the patient 80 decreases, the target water-remove rate decreases; and that as the pressoreceptor-reflex sensitivity of the patient 80 decreases, the target water-remove rate decreases. Thus, a patient who has arteriosclerosis can be effectively prevented from falling in a shock during a dialysis operation, and water can be quickly removed from blood of the patient, without causing an abrupt blood-pressure decrease in the patient.

In the illustrated embodiment, the target-water-remove-rate determining means 110 determines the target water-remove rate range based on the actual autonomic-nerve-activity-related information, according to the prescribed relationship, as shown in FIG. 5, that is expressed by a multi-dimensional coordinate system defined by an axis of abscissa representative of autonomic-nerve-activity-related information and an axis of ordinate representative of water-remove rate, so that water can be removed as quickly as possible from blood of the patient, without causing the patient to fall in a shock. Thus, water can be quickly removed from a patient having arteriosclerosis, without causing an abrupt blood-pressure decrease in the patient.

While the present invention has been described in detail in its preferred embodiment, by reference to the drawings, the invention may otherwise be embodied.

For example, in the illustrated embodiment, the autonomic-nerve-activity-related information that is related to the degree of arteriosclerosis is obtained as the low-frequency component of fluctuations of the blood-pressure values, the high-frequency component of fluctuations of the pulse periods, or the pressoreceptor-reflex sensitivity as the ratio of the high-frequency component to the low-frequency component. However, any other known parameter that reflects autonomic-nerve activity may be employed.

In the illustrated embodiment, the target-water-remove-rate determining means 110 determines the target water-remove rate range. However, in the case where the water-remove-rate dial 52b for manually adjusting the water-remove rate in a certain range is not employed, the determining means 110 may be modified to determine a target water-remove rate.

The illustrated dialyzing apparatus 4 employs the blood-pressure determining means 92 for determining the blood-pressure values. However, the determining means 92 may not be employed.

In the illustrated embodiment, the pulse-wave propagation velocity PWV is determined based on the pulse-wave propagation time DT equal to the time difference between the R-wave of the electrocardiographic waveform represented by the electrocardiograph signal SE and the rising point of the photoelectric pulse wave represented by the photoelectric-pulse-wave signal SM2. However, the pulse-wave propagation velocity PWV may be determined based on a pulse-wave propagation time DT equal to a time difference between a second heart sound II and a rising point of a pressure pulse wave detected by a pressure-pulse-wave sensor from an artery of a prescribed portion of a patient.

It is to be understood that the present invention may be embodied with other changes, improvements and modifications that may occur to a person skilled in the art without departing from the spirit and scope of the invention.

What is claimed is:

1. A dialyzing apparatus comprising:
    a dialyzer which removes water from blood of a patient at a pre-set water-remove rate;
    an autonomic-nerve-activity-related-information obtaining device which obtains autonomic-nerve-activity-related information that is related to an activity of an autonomic nerve of the patient, the autonomic-nerve-activity-related information being any one of (a) a low-frequency component of fluctuations of blood-pressure values of the patient, (b) a high-frequency component of fluctuations of pulse-period values of the patient, and (c) a pressoreceptor-reflex sensitivity defined as a ratio of one of the low-frequency component and the high-frequency component to the other of the two components;
    a target-water-remove-rate determining means for determining a target-water-remove rate based on autonomic-nerve-activity-related information obtained by the autonomic-nerve-activity-related-information obtaining device; and
    a water-remove-rate display device which displays the target water-remove rate determined by the target-water-remove-rate determining means;
    wherein the water-remove rate of the dialyzer is set by an operator to a desired water-remove rate in view of the target water-remove rate displayed by the water-remove-rate display device.

2. A dialyzing apparatus comprising:
    a dialyzer which removes water from blood of a patient at a pre-set water-remove rate;
    an autonomic-nerve-activity-related-information obtaining device which obtains autonomic-nerve-activity-related information that is related to an activity of an autonomic nerve of the patient, the autonomic-nerve-activity-related information being any one of (a) a low-frequency component of fluctuations of blood-pressure values of the patient (b) a high-frequency component of fluctuations of pulse-period values of the patient, and (c) a pressoreceptor-reflex sensitivity defined as a ratio of one of the low-frequency component and the high-frequency component to the other of the two components;
    a water-remove-rate changing means for changing the pre-set water-remove rate to a target water-remove rate based on the autonomic-nerve-activity-related information obtained by the autonomic-nerve-activity-related-information obtaining device; and
    a dialyzer control device which operates the dialyzer at the target water-remove rate established by the water-remove-rate changing means.

3. A dialyzing apparatus according to claim 2, further comprising a target-water-remove-rate determining means for determining the target water-remove rate based on the autonomic-nerve-activity-related information obtained by the autonomic-nerve-activity-related-information obtaining device, wherein the water-remove-rate changing means changes the pre-set water-remove rate to the target water-remove rate determined by the target-water-remove-rate determining means.

4. A dialyzing apparatus according to claim 3, wherein the target-water-remove-rate determining means determines a target water-remove rate range based on the autonomic-nerve-activity-related information comprising at least one of a low-frequency component of fluctuations of blood-pressure values of the patient, a high-frequency component of fluctuations of pulse-period values of the patient, and a pressoreceptor-reflex sensitivity defined as a ratio of one of the low-frequency component and the high-frequency component to the other of the low-frequency component and the high-frequency component, and wherein the water-remove-rate changing means changes the pre-set water-remove rate to a value falling within the determined target water-remove-rate range.

5. A dialyzing apparatus according to claim 4, wherein the target-water-remove-rate determining means determines a lower target water-remove rate range based on the autonomic-nerve-activity-related information comprising at least one of a greater low-frequency component of fluctuations of blood-pressure values of the patient, a smaller high-frequency component of fluctuations of pulse-period values of the patient, and a smaller pressoreceptor-reflex sensitivity of the patient.

6. A dialyzing apparatus according to claim 4, wherein the target-water-remove-rate determining means determines, in a two-dimensional coordinate system which is defined by a first axis indicative of autonomic-nerve-activity-related information and a second axis indicative of water-remove rate, the target water-remove rate range based on the obtained autonomic-nerve-activity-related information according to a predetermined relationship between autonomic-nerve-activity-related information and water-remove rate range.

7. A dialyzing apparatus according to claim 1, wherein the target-water-remove-rate determining means determines a target water-remove rate range based on the autonomic-nerve-activity-related information comprising at least one of a low-frequency component of fluctuations of blood-pressure values of the patient, a high-frequency component of fluctuations of pulse-period values of the patient, and a pressoreceptor-reflex sensitivity defined as a ratio of one of the low-frequency component and the high-frequency component to the other of the low-frequency component and the high-frequency component, and wherein the water-remove-rate display device displays the determined target water-remove rate range.

8. A dialyzing apparatus according to claim 7, wherein the target-water-remove-rate determining means determines a lower target water-remove rate corresponding to the autonomic-nerve-activity-related information comprising at least one of a smaller low-frequency component of fluctuations of blood-pressure values of the patient, a greater high-frequency component of fluctuations of pulse-period values of the patient, and a smaller pressoreceptor-reflex sensitivity of the patient.

9. A dialyzing apparatus according to claim 1, wherein the target-water-remove-rate determining means determines, in a two-dimensional coordinate system which is defined by a first axis indicative of autonomic-nerve-activity-related information and a second axis indicative of water-remove rate, the target water-remove rate range based on the obtained autonomic-nerve-activity-related information according to a pre-determined relationship between autonomic-nerve-activity-related information and water-remove rate range.

10. A dialyzing apparatus according to claim 1, further comprising:
    a water-remove-rate setting device which is operable by an operator to set a desired water-remove rate in view of the target water-remove rate displayed by the water-remove-rate display device; and
    a dialyzer control device which operates the dialyzer at the desired water-remove rate set through the water-remove-rate setting device.

11. A dialyzing apparatus according to claim 7, further comprising:
    a water-remove-rate setting device which is operable by an operator to set a desired water-remove rate that falls within the target water-remove rate range displayed by the water-remove-rate display device; and
    a dialyzer control device which operates the dialyzer at the desired water-remove rate set through the water-remove-rate setting device.

12. A dialyzing apparatus comprising:
    a dialyzer which removes water from blood of a patient at a pre-set water-remove rate;
    an autonomic-nerve-activity-related-information obtaining device which obtains autonomic-nerve-activity-related information that is related to an activity of an autonomic nerve of the patient;
    a target-water-remove-rate determining means for determining, in a two-dimensional coordinate system which is defined by a first axis indicative of autonomic-nerve-activity-related information and a second axis indicative of water-remove rate, the target water-remove rate range based on the obtained autonomic-nerve-activity-related information according to a pre-determined relationship between autonomic-nerve-activity-related information and water-remove rate range; and
    a water-remove-rate display device displays the target-water-remove rate range determined by the target-water-remove-rate determining means;
    wherein the water-remove rate of the dialyzer is set by an operator to a desired value in view of the target water-remove rate range displayed by the water-remove-rate display device.

* * * * *